(12) United States Patent
Roederer et al.

(10) Patent No.: US 9,701,634 B2
(45) Date of Patent: Jul. 11, 2017

(54) PROCESS FOR THE SYNTHESIS OF 3-METHYL-PYRIDINE

(75) Inventors: Detlef Roederer, Brig (CH); Daniel Zollinger, Sierre (CH); Jean-Yves De Riedmatten, Uvrier (CH)

(73) Assignee: LONZA LTD, Basel (CH)

( * ) Notice: Subject to any disclaimer, the term of this patent is extended or adjusted under 35 U.S.C. 154(b) by 999 days.

(21) Appl. No.: 12/822,770

(22) Filed: Jun. 24, 2010

(65) Prior Publication Data

US 2011/0003997 A1 Jan. 6, 2011

Related U.S. Application Data

(60) Provisional application No. 61/219,951, filed on Jun. 24, 2009.

(30) Foreign Application Priority Data

Jun. 24, 2009 (EP) .................................... 09008251

(51) Int. Cl.
C07D 213/10 (2006.01)
(52) U.S. Cl.
CPC .................................. C07D 213/10 (2013.01)
(58) Field of Classification Search
CPC .................................................... C07D 213/10
See application file for complete search history.

(56) References Cited

U.S. PATENT DOCUMENTS 2,700,042 A 1/1955 Aries
4,337,342 A * 6/1982 Dinkel .......................... 546/251

FOREIGN PATENT DOCUMENTS

FR 2161128 7/1973
GB 01005984 A 9/1965

OTHER PUBLICATIONS

Tea Swee Sin "A Comparative Study on the Jet Loop Reactor and Continuos Stirred Tank Reactor in the Selective Hydrogenation of Palm Olein (I.V.64)" Thesis Universiti Teknologi Malaysia May 2005.*
Dierendonck "Loop Venturi Reactors a Feasible Alternative to Stirred Tank Reactors?"Ind. Eng. Chem. Res. 1998, 37, 734-738.*
Grayson et al., "An Improved Liquid-Phase Synthesis of Simple Alkylpyridines", Helvetica Chimica Acta, vol. 67, pp. 2100-2110; 1984.
J.I. Grayson, R. Dinkel: "244. An Improved Liquid-Phase Synthesis of Simple Alkylpyridines," Halvetica Chimica Acta, vol. 67, No. 8, 1984, pp. 2100-2110, XP002548839, cited in the application tables 1-3.
M.I. Farberov et al.: "Synthesis of pyridine compounds from paraldehyde and ammonia," Zhurnal Prikladnoi Khimii, vol. 37, No. 3, 1964, pp. 661-668, XP009123706, p. 662.
International Search Report and International Preliminary Report on Patentability corresponding to International Application No. PCT/EP2010/003773 dated Apr. 19, 2011.

* cited by examiner

*Primary Examiner* — David K O'Dell
(74) *Attorney, Agent, or Firm* — Hoffmann & Baron, LLP

(57) ABSTRACT

The present invention discloses a process for the synthesis of 3-methyl-pyridine from formaldehyde, paracetaldehyde, ammonia and acetic acid, whereby said compounds are reacted and said process comprises the following parameters:
  a) a reaction temperature of 260-300° C.;
  b) a molar ratio of formaldehyde and paraldehyde (calculated as acetaldehyde) of 0.7-1.4 mol/mol:
  c) an ammonia concentration of 10-20 weight-%
  d) an acetic acid concentration of 4-20 weight-%
  e) a paraldehyde (calculated as acetaldehyde) concentration of 0.4-1.6 Mol/kg
  f) a retention time of 10-30 minutes in case of a continuous reaction and 10-90 minutes in case of a discontinuous reaction; and
  g) a reaction pressure of 30-130 bar.

6 Claims, No Drawings

PROCESS FOR THE SYNTHESIS OF 3-METHYL-PYRIDINE

This application is based on, and Applicant claims priority from, United States Provisional Application bearing Ser. No. 61/219,951 filed Jun. 24, 2009, and European Patent Application bearing Serial No. EP 09008251.2 filed Jun. 24, 2009, both of which are incorporated herein by reference.

BACKGROUND OF THE INVENTION

The present invention concerns a process for the production of 3-methyl-pyridine (3-picoline) from formaldehyde, paraldehyde, ammonia, and acetic acid.

3-picoline is a colourless, flammable liquid which is used as a solvent, for the production of medicaments and insecticides as well as for the synthesis of nicotinic acid and nicotine amide.

Several synthetic routes for the production of 3-picoline are known in the art, which are generally based on an addition/cyclization reaction of aldehyde/ketone mixtures with an ammonia compound. Said reactions can run in the gas phase or in the liquid phase as well as using a catalyst.

The process according to the present invention is based on the publication of Grayson, J. and Dinkel, R., "An improved Liquid-Phase Synthesis of Simply Alkylpyridines", *Helvetica Chimica Acta*, Vol. 67 (1984), p. 2100-2110.

The authors of this publication describe in table 2, p. 2108 inter alia the synthesis of 3-picoline from acetaldehyde and formaldehyde, whereby different ammonia sources are compared with regard to 3-picoline yield as well as to the presence of diverse, unwanted side products.

In particular, it is shown that the use of ammonia acetate results in a yield of 44%, whereby 3 ethylpyridine as the main side product is present in an amount of 18%.

Thus. the technical problem to be solved is to improve the process of Grayson and Dinkel with regard to 3-picoline yield, reduction of 3-ethylpyridine amount as main side product as well as an increase in the space/time yield.

DESCRIPTION OF THE INVENTION

Said problem is surprisingly solved by the process according to the present invention for the synthesis of 3-methyl-pyridine from formaldehyde, paraldehyde (trimeric acetaldehyde. 2,4,6-trimethyl-1,3,5-trioxane). ammonia and acetic acid, whereby said compounds are reacted and said process comprises the following parameters:
  a) a reaction temperature of 260-300° C.;
  b) a molar ratio of formaldehyde and paraldehyde (calculated as acetaldehyde) of 0.7-1.4 mol/mol:
  c) an ammonia concentration of 10-20 weight-%
  d) an acetic acid concentration of 4-20 weight-%
  e) a paraldehyde (calculated as acetaldehyde) concentration of 0.4-1.6 Mol/kg
  f) a retention time of 10-30 minutes in case of a continuous reaction and 10-90 minutes in case of a discontinuous reaction; and
  g) a reaction pressure of 30-130 bar.

It may be preferred that the reaction takes place in a reactor. More preferably, said reactor is a system with a high efficiency of mixing like stirring devices as well as continuous flow-through stirrer vessels and discontinuous stirrer vessels. Most preferably, said reactor is a loop-reactor or jet-loop-reactor.

Loop- and jet-loop-reactors according to the invention are characterized by the fact that the respective reactants are brought to reaction with the catalyst-solution in a continuous manner. One major advantage of jet-loop-reactors compared to stirrer vessels for the production of 3-picoline is the more intensive and faster mixing of fluids when operating under a high circulation stream, resulting in an increased passage of heat and material. Preferably, the process according to the invention is operated in a loop reactor with stream zones. Another advantage of stream-powered loop reactors is a finer dispersion of the added phases and thus a bigger specific interphase.

Furthermore, it may be preferred that side products are removed in the process of re-cycling the catalyst. Generally, all technical means known in the art can be employed, like e.g. extraction and rectification. Especially preferred is distillation.

The process according to the invention contemplates the addition of ammonia and formaldehyde both in molecular form as well as in form of their addition product hexamethylene-tetramine (Urotropine).

The process according to the invention is distinguished from the prior art according to Dinkel et al. inter alia by combining a higher selectivity with regard to the formation of 3-methylpyridine with an increased space/time yield. This results in a major technical advantage, since normally an increased space/time yield results in a decrease in selectivity.

The process according to the present invention is further explained by the following, non-limiting example.

EXAMPLE 1

The reaction took place continuously in a 100 Liter jet loop reactor with a very high degree of mixing. Pumps were used to add the catalyst solution (a mixture of water, ammonia and acetic acid) and the educts (paraldehyde and formalin).

261 kg/h of catalyst solution (75 weight-% water. 15 weight-% ammonia and 10 weight-% acetic acid) were brought into the reactor via high-pressure pumps. Simultaneously. 13 kg/h paracetaldehyde and 26.8 kg/h formalin solution (37.4 weight-%) are were added continuously via high-pressure pumps. The reactor temperature is was kept at 278° C. and the reactor pressure at 100 bar. A retention time of 20 minutes results resulted in a crude solution containing 10.02 kg/h 3 picoline and 0.37 kWh 3-ethylpyridine. Under these conditions, a 3 picoline yield of 64.6% (based on formaldehyde) and a 3-ethylpyridine yield of 3.5% (based on acetaldehyde) is were achieved. All pyridine bases were analyzed via gas chromatography.

The invention claimed is:

1. A continuous process for the synthesis of 3-methyl-pyridine from formaldehyde, paraldehyde, ammonia and acetic acid, comprising continuously subjecting said compounds in a jet loop reactor to reaction conditions comprising the following parameters:
  a) a reaction temperature of 260-300° C.;
  b) a molar ratio of formaldehyde and paraldehyde (calculated as acetaldehyde) of 0.7-1.4 mol/mol;
  c) an ammonia concentration of 10-20 weight-%
  d) an acetic acid concentration of 4-20 weight-%
  e) a paraldehyde (calculated as acetaldehyde) concentration of 0.4-1.6 Mol/kg
  f) a retention time of 10-30 minutes; and
  g) a reaction pressure of 30-130 bar; whereby the space/time yield of 3-methylpyridine is more than 50 kg/m3*h, and the 3-methylpyridine yield is at least 64% (based on formaldehyde) and the 3-ethylpyridine yield is at most 4% (based on paraldehyde).

2. A process according to claim 1, whereby said process takes place in a reactor system with a high efficiency of mixing.

3. Process according to claim 1, whereby side products are removed in the process of re-cycling the catalyst.

4. Process according to claim 3, whereby said side products are removed via rectification or extraction.

5. Process according to claim 1, whereby the space/time yield of 3-methylpyridine is more than 80 kg/m3*h.

6. Process according to claim 1, whereby the space/time yield of 3-methylpyridine is more than 100 kg/m3*h.

\* \* \* \* \*